United States Patent [19]

Mackay et al.

[11] 4,341,112
[45] Jul. 27, 1982

[54] MEASUREMENT OF SOIL MOISTURE

[75] Inventors: Neilson A. M. Mackay, John C. Beal, both of Kingston, Ontario, Canada

[73] Queen's University at Kingston, Ontario, Canada

[21] Appl. No.: 162,093

[22] Filed: Jun. 23, 1980

[30] Foreign Application Priority Data

Jun. 22, 1979 [CA] Canada .................................. 330390

[51] Int. Cl.³ .......................................... G01N 27/02
[52] U.S. Cl. .................................................. 73/73
[58] Field of Search ............................... 73/73, 336.5

[56] References Cited

U.S. PATENT DOCUMENTS

| | | | |
|---|---|---|---|
| 2,793,527 | 5/1957 | Turner, Jr. et al. | 73/73 |
| 2,985,827 | 5/1961 | Hasenkamp | 73/73 |
| 3,045,198 | 7/1962 | Dolan et al. | 73/73 |
| 3,550,439 | 12/1970 | Hollies et al. | 73/73 |
| 4,091,367 | 5/1978 | Harman | 333/237 |
| 4,137,931 | 2/1979 | Hasenbeck | 73/73 |
| 4,224,607 | 9/1980 | Poirier | 333/237 |

FOREIGN PATENT DOCUMENTS

| | | | |
|---|---|---|---|
| 232596 | 4/1966 | U.S.S.R. | 73/73 |
| 246154 | 11/1969 | U.S.S.R. | 73/73 |

Primary Examiner—Donald O. Woodiel
Attorney, Agent, or Firm—Lowe, King, Price & Becker

[57] ABSTRACT

A method and apparatus for measuring the moisture content of bulk material which involves placing a length of leaky co-axial cable in the bulk material so as to be buried therein and spaced from an electro-magnetic sensor in the region of interest. A signal of high frequency electro-magnetic energy is injected into the cable, and at least one of phase and time of arrival of the signal at the sensor with respect to the injected signal is measured and therefrom the moisture content of the material determined. The electro-magnetic sensor is preferably a second leaky co-axial cable buried in the bulk material and spaced a selected distance from the first coaxial cable and parallel thereto. The spacing therebetween the coaxial cables is in the range of one to fifty feet and the frequency of the electro-magnetic energy is in the range of 20–500 MHz.

7 Claims, 5 Drawing Figures

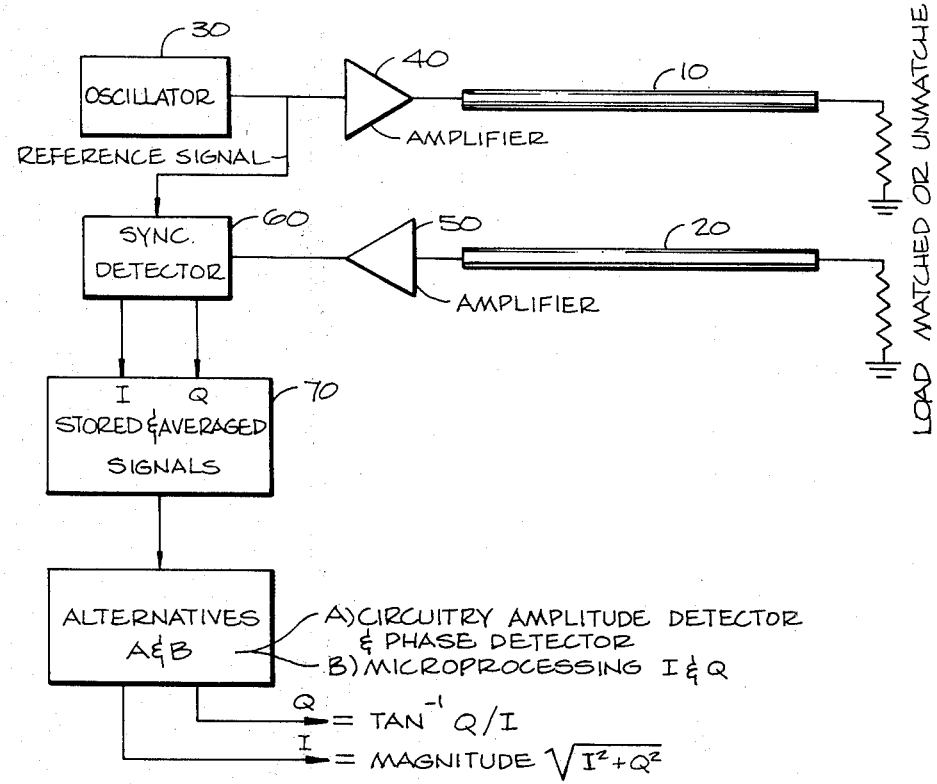
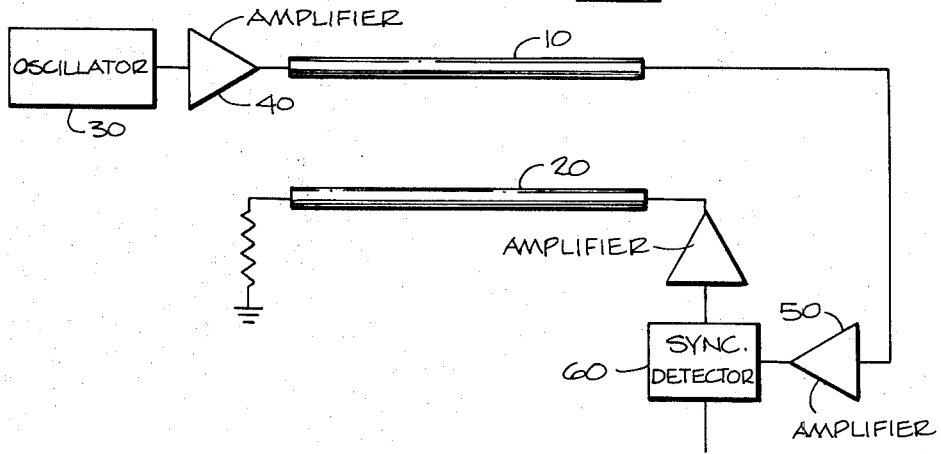

MEASUREMENT OF SOIL MOISTURE

This invention relates to measuring the moisture content of bulk material and particularly to measuring field moisture content or grain stored in bulk. The invention has particular application in an agricultural environment.

It is known that the moisture content of a material can be determined by measuring the attenuation of high frequency electromagnetic waves in the material. The known proposals however, are relevant to laboratory size samples or controlled indoor factory production or processing of such items as paper sheet, tobacco leaves or other objects having closely controlled shape and/or dimension. The known systems are incapable of extension to an external environment for moisture measurement of bulk material covering a large area or having a large volume.

An object of the present invention is to provide means for economically measuring moisture content, or monitoring change of moisture content or determining or monitoring moisture distribution in material of considerable bulk, for example, an agricultural field or stored grain.

In accordance with the present invention, electromagnetic energy is transmitted by a length of leaky coaxial cable transmission line buried in the bulk substance whose moisture content is to be measured. Some of the electromagnetic energy travelling along the cable "leaks out" of the cable and travels as an external field, partially guided by the direction of the cable. A second coaxial cable buried in the bulk material and spaced from the first coaxial cable serves as an antenna monitoring the field generated in the material. Measurement of one of time delay and phase change of the received signal relative to the transmitted signal provides an indication of moisture content. The measurement of moisture content is based on the fact that the dielectric constant of substances vary considerably with moisture. A change in dielectric constant causes a change in propagation velocity of the injected energy.

The invention is illustrated by way of example with reference to the accompanying drawings wherein:

FIGS. 3 and 4 are diagrammatic schematics illustrating arrangements for measuring moisture in a selected volume.

Figure 1:
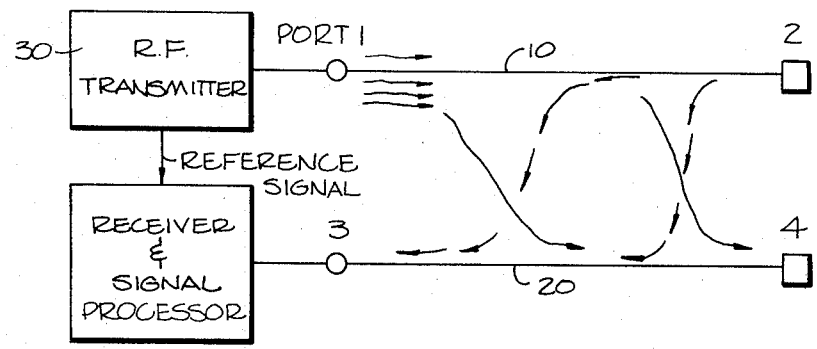
FIG. 1 is a diagrammatic schematic view of an arrangement for measuring the moisture content of the soil in a long section of a field.

FIG. 1 shows a situation in which the moisture content of the soil of a long section of field is to be measured. Two leaky coaxial cables 10 and 20 are laid several feet apart (from one foot to 25 feet or more) and buried about a foot deep in the soil. Into cable 10, a radio frequency (RF) oscillator 30 injects a continuous waveform at port 1 and much of the energy is absorbed in an RF termination at port 2. A portion of the injected energy leaks into the medium and some of this is coupled into the second cable 20. Due to perturbations in each cable and the natural inconsistency of most media, reflected waves are induced at all points along the cables and produce a small reflected signal which is received at port 3. By comparing the phase of the signal entering at port 1 and returning at port 3, a measure of the average velocity of propagation can be obtained. Often of more importance, a change in this phase is useful to measure the change in velocity of propagation and hence the change in dielectric constant and ultimately moisture content.

An important version of this technique can be obtained if the injected signal at port 1 is a pulsed radio frequency waveform, in which case the reflection from each point along the cable returns to port 3 at a unique time. This therefore provides moisture information on a point by point basis along the sensor instead of the average reading obtained in the continuous case discussed above.

Figure 2:
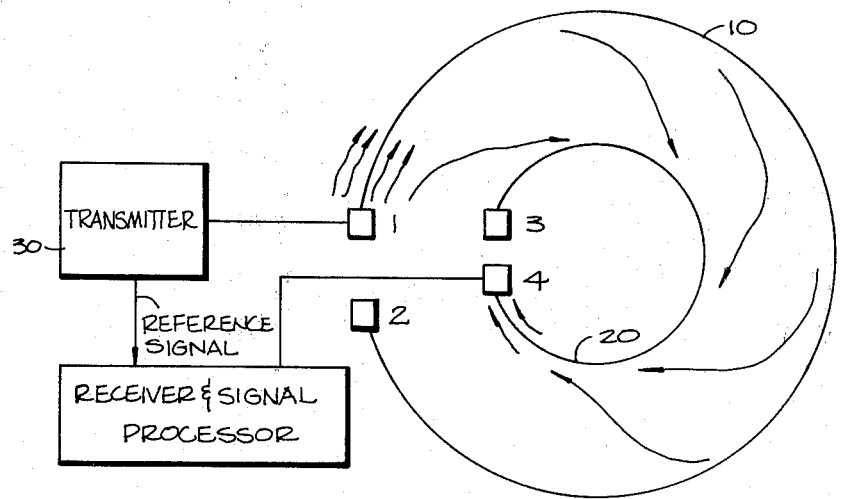
FIG. 2 illustrates an arrangement for measuring moisture content of an enclosed region.

Another illustration of the technique is shown in FIG. 2. In this case the transmission leaky cable 10 is again buried in the medium under test but now encloses a region of interest and the other EM sensor, either a short section of buried leaky cable 20 as shown or dipole close to the ground, is positioned near the centre of the enclosed area. Again, radio frequency energy is injected into port 1 and travels to port 2 where it is absorbed in a termination. Some of the leaked energy travels to the central monitoring point by way of the medium under test and its phase of time of arrival measured with respect to the transmitted signal. As before, a change in moisture content of the medium produces a change in the velocity of propagation through the medium, thereby producing a change in the time of arrival or phase of the received waveform. In a similar manner to the pulse system described above, if a pulse signal is injected at port 1, the moisture content of wedge shaped pieces of the medium can be measured, the size of the wedges being dependent on the pulse width.

In FIG. 3 there is illustrated an arrangement for measuring moisture content in a selected volume. An oscillator signal generator 30 of 20-50 MHz (preferably 60 MHz) injects a signal via signal amplifier 40 into a length of leaky coaxial cable 10 buried in the material whose moisture content is to be measured. Extending parallel to and spaced from cable 10 is a second leaky coaxial cable 20. The signals received by cable 20 are amplified by amplifier 50 and fed to a sync detector 60 provided with a reference signal directly from the oscillator signal generator 40. Outputs I and Q of the sync detector 60 are stored and averaged over a long period by a micro-processor 70 and the output therefrom processed either by suitable circuitry (amplitude and/or phase detector) or a micro-processor. The outputs from these provide directly or though suitable conversion the average moisture content of the volume of soil between cables 10 and 20. The free ends of the cables in this arrangement may have a matched or unmatched load connected thereto.

A second arrangement for measuring moisture content in a selected volume is illustrated in FIG. 4. In this arrangement the free ends of leaky coaxial cables 10 and 20 have matched loads and are connected via respective signal amplifiers 40 and 50 to the sync detector 60.

Figure 5:
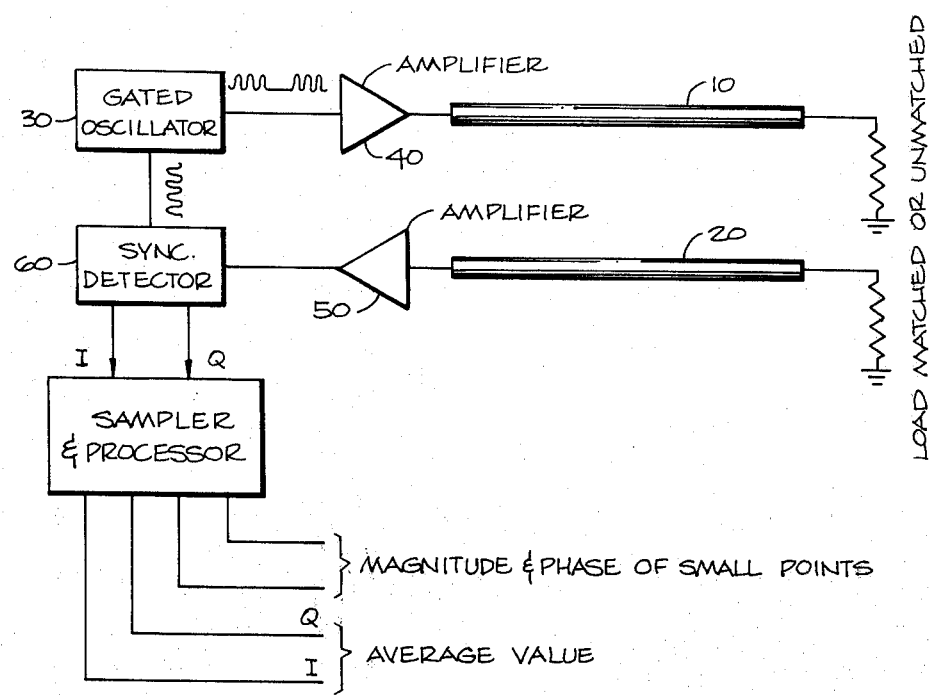
FIG. 5 is a diagrammatic schematic of an arrangement for a specific measurement.

The arrangement illustrated in FIG. 5 is for measuring moisture content of specific locations in the over-all area. The arrangement is substantially the same as in FIG. 3 except that the signal injected into leaky coaxial cable 10 is a pulsed waveform as briefly described previously providing moisture information on a point by point basis.

Particulars of the electronics and detailed circuits have not been described herein as such is well within the capabilities of any electronics technician or anyone else skilled in such art and utilizing common general knowledge.

We claim:

1. A method of measuring the moisture content of bulk material comprising:
    (a) placing a length of leaky co-axial cable in the bulk material so as to be buried therein and spaced from an electro-magnetic sensor in the region of interest;
    (b) injecting a signal of high frequency electro-magnetic energy into the cable; and
    (c) measuring at least one of phase and time of arrival of the signal at the sensor with respect to the injected signal and therefrom determine the moisture content of the material.

2. The method of claim 1 wherein said electro-magnetic sensor includes a second leaky co-axial cable buried in the bulk material.

3. The method of claim 1 wherein said leaky co-axial cables are placed parallel to one another with a space therebetween in the range of one to fifty feet.

4. The method of claim 1 wherein said leaky co-axial cables have a space therebetween in the range of 20 to 30 feet.

5. The method of claim 1 wherein the frequency of the electro-magnetic energy is in the range of 20–500 MHz.

6. The method of claim 1 wherein the signal injected is a pulsed signal.

7. Apparatus for measuring the moisture content of bulk material comprising:
    (a) a first and second separate length of leaky co-axial cable which in use are buried in the bulk material in spaced apart relation relative to one another;
    (b) means for injecting a high frequency electro-magnetic energy signal into one of said cables; and
    (c) means to measure at least one of phase and time of arrival of the signal received by the second cable relative to the injected signal.

* * * * *